(12) United States Patent
McIvor et al.

(10) Patent No.: US 6,360,888 B1
(45) Date of Patent: Mar. 26, 2002

(54) GLUCOSE SENSOR PACKAGE SYSTEM

(75) Inventors: K. Collin McIvor, Claremont; James L. Cabernoch, Santa Clarita; Kevin D. Branch, Northridge; Nannette M. Van Antwerp; Edgardo C. Halili, both of Valencia; John J. Mastrototaro, Los Angeles, all of CA (US)

(73) Assignee: Minimed Inc., Northridge, CA (US)

( * ) Notice: Subject to any disclaimer, the term of this patent is extended or adjusted under 35 U.S.C. 154(b) by 0 days.

(21) Appl. No.: 09/501,848

(22) Filed: Feb. 10, 2000

Related U.S. Application Data (60) Provisional application No. 60/121,655, filed on Feb. 25, 1999.

(51) Int. Cl.[7] .................. B65D 85/38; B65D 83/10; B65D 85/00; A61B 17/06; A61B 5/05
(52) U.S. Cl. .................. 206/305; 206/306; 206/438; 206/363; 206/459.1; 600/347; 600/345; 600/365
(58) Field of Search ................. 600/345, 347, 600/357, 309; 204/403, 411, 412; 206/438, 363, 306, 459.1, 305

(56) References Cited

U.S. PATENT DOCUMENTS

| | | | |
|---|---|---|---|
| 4,057,029 A | * 11/1977 | Seiter | ................. 116/114 |
| 4,655,880 A | 4/1987 | Liu | |
| 5,171,689 A | * 12/1992 | Kawaguri et al. | .......... 435/290 |
| 5,299,571 A | 4/1994 | Mastrototaro | |
| 5,322,063 A | * 6/1994 | Allen et al. | .................. 600/347 |
| 5,344,017 A | 9/1994 | Wittrock | |
| 5,384,028 A | 1/1995 | Ito | |
| 5,390,671 A | 2/1995 | Lord et al. | |
| 5,476,792 A | 12/1995 | Ezrielev et al. | |
| 5,985,129 A | * 11/1999 | Gough et al. | ................ 600/347 |
| 6,091,975 A | * 7/2000 | Daddona et al. | ............ 600/345 |
| 6,103,033 A | 8/2000 | Say et al. | |
| 6,134,461 A | * 10/2000 | Say et al. | .................... 600/345 |
| 6,175,752 B1 | 1/2001 | Say et al. | |

FOREIGN PATENT DOCUMENTS

| | | | |
|---|---|---|---|
| DE | 4331934 | 5/1993 | .......... A61M/5/168 |
| EP | 0326081 | 8/1989 | ............ C12M/1/40 |
| WO | 9838112 | 9/1998 | .......... B65D/79/02 |
| WO | 9842252 | 10/1998 | ............ A61B/5/00 |

* cited by examiner

*Primary Examiner*—John P. Lacyk
*Assistant Examiner*—Navin Natnithithadha
(74) *Attorney, Agent, or Firm*—Minimed Inc.

(57) ABSTRACT

A glucose sensor package system that includes a glucose sensor and a protective package that indicates exposure to temperature changes to indicate proper temperature control. Also covered are methods of transporting and sterilizing the package. In addition, glucose sensors directed to various sizing and positioning of the electrodes on the glucose sensor are covered.

64 Claims, 6 Drawing Sheets

IMPORTANT NOTE
USE GLUCOSE SENSORS ONLY IF:
- THE STERILIZATION INDICATOR DOT ( 🟡 ) IS REDDISH/ORANGE, NOT MUSTARD YELLOW.
- THE TEMPERATURE DOT ( ○ ) IS CLEAR, NOT BLACK.

GLUCOSE SENSOR PACKAGE SYSTEM

RELATED APPLICATIONS:

This application claims priority on U.S. Provisional Patent Application Ser. No. 60/121,655, filed Feb. 25, 1999, which is herein incorporated by reference in its entirety, including all attachments.

FIELD OF THE INVENTION

This invention relates to glucose monitor systems and, in particular embodiments, to glucose sensors for use with glucose monitor systems and to the packaging for the glucose sensors. The invention also relates to the size, shape and positioning of electrodes on a glucose sensor.

BACKGROUND OF THE INVENTION

Over the years, bodily characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in the subcutaneous tissue. The pain of lancing and the cumulative discomfort from multiple needle pricks is a strong reason why patients fail to comply with a medical testing regimen used to determine a change in characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors are being developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571.

Many of these glucose sensors utilize complex chemical structures and/or reactions that can degrade over time, if maintained under improper conditions. Since sensors may be stored for long periods of time after manufacture and prior to use, the sensors must be monitored frequently and maintained in areas with a carefully controlled environment. The monitoring of sensors is particularly difficult once the sensors have been sterilized and placed in packages. Often the only way to monitor the sensors is to pull a sample and remove it from a package. However, this destroys the sterility and results in waste. Also, monitoring sensors that have been shipped to a user are problematic or difficult.

SUMMARY OF THE DISCLOSURE

It is an object of an embodiment of the present invention to provide an improved glucose sensor package system, which obviates for practical purposes, the above mentioned limitations.

Embodiments of the present invention are directed to a glucose sensor package system that includes a glucose sensor and a protective package that indicates proper exposure to sterilization or exposure to temperature changes to indicate proper temperature control. Also covered are methods of transporting and sterilizing the package. In addition, further embodiments of the glucose sensors are directed to the sizing and positioning of the electrodes on the glucose sensor.

According to an embodiment of the invention, a glucose sensor package system for storing and transporting a glucose sensor includes at least one glucose sensor, a protective package and at least one temperature exposure indicator. The protective package has an interior to hold the at least one glucose sensor in the interior of the protective package. The at least one temperature exposure indicator is used to determine if the protective package has been exposed to at least one exposure temperature relative to a predetermined threshold temperature value. In particular embodiments, the at least one exposure temperature is above the predetermined threshold temperature, and the at least one temperature exposure indicator indicates when there has been exposure to the at least one exposure temperature. For instance, the predetermined threshold temperature is 75° F. and the at least one exposure temperature exceeds 75° F., or the predetermined threshold temperature is 100° F. and the at least one exposure temperature exceeds 100° F. In other embodiments, the at least one exposure temperature is below the predetermined threshold temperature, and the at least one temperature exposure indicator indicates when there has been exposure to the at least one exposure temperature. For instance, the predetermined threshold temperature is 36° F. and the at least one exposure temperature is below 36° F.

In additional embodiments, the at least one temperature exposure indicator indicates when the at least one exposure temperature relative to the predetermined threshold temperature existed for a predetermined period of time. For instance, the predetermined period of time can be at least 10 minutes, or at least 60 minutes. In other embodiments, the period of time is established as a function of a magnitude of a difference between the at least one exposure temperature and the predetermined threshold temperature.

In particular embodiments, the at least one temperature exposure indicator is attached to the protective package. For instance, the at least one temperature exposure indicator may be attached to the interior of the protective package or an exterior of the protective package. In further embodiments, the at least one temperature exposure indicator is contained within the protective package, or attached to the glucose sensor. In preferred embodiments, the at least one temperature exposure indicator is a sticker. Other embodiments are directed to a method of transporting the glucose sensor in a package system.

According to another embodiment of the invention, a glucose sensor package system for storing and transporting a glucose sensor includes at least one glucose sensor, a protective package, and at least one temperature exposure indicator. The protective package has an interior within which the at least one glucose sensor is disposed, and an exterior. The at least one temperature exposure indicator has first and second states, of which the first state indicates that the protective package has not been exposed to at least one exposure temperature relative to a predetermined threshold temperature value, and the second state indicates that the protective package has been exposed to the at least one exposure temperature. The at least one temperature exposure indicator, in particular embodiments, is attached to the interior of the protective package or the exterior of the protective package, is contained within the protective package, or is attached to the glucose sensor.

In further particular embodiments, the glucose sensor package system includes a plurality of glucose sensors, each of which is enclosed within a separate package. The plurality of separately packaged glucose sensors in turn are disposed within the interior of the protective package. In more specific embodiments, the glucose sensor package system includes a plurality of the at least one temperature exposure indicators, each of which is attached to one of the separate packages.

In further embodiments, the glucose sensor package system includes a plurality of the at least one temperature exposure indicators, each of which provides an indication of exposure to at least one exposure temperature relative to a different predetermined threshold temperature value. These embodiments afford more precise indications of a maximum temperature to which the package system has been exposed.

Another embodiment of the present invention is directed to a method of transporting a glucose sensor. The method includes the steps of providing at least one glucose sensor. Providing a protective package having an interior. Holding the at least one glucose sensor in the interior of the protective package. Using at least one temperature exposure indicator to determine if the protective package has been exposed to at least one exposure temperature relative to a predetermined threshold temperature value.

A further embodiment of the present invention is directed to a method of transporting a glucose sensor, the method including the steps of providing a glucose sensor package system. The package system including at least one glucose sensor, a protective package having an interior within which the at least one glucose sensor is disposed and an exterior, and at least one temperature exposure indicator having first and second states. Transporting the glucose sensor package system, and observing the state of the at least one temperature exposure indicator to determine if the protective package has been exposed to the at least one exposure temperature during transport.

Additional embodiments of the method employ a glucose sensor package system that includes a plurality of the at least one temperature exposure indicators, each of which provides an indication of exposure to at least one exposure temperature relative to a different predetermined threshold temperature value. In these embodiments, the observing step includes an observation of the state of each of the at least one temperature exposure indicators to determine if the protective package has been exposed to at least one exposure temperature relative to at least one of the different predetermined threshold values.

Another embodiment of the present invention is directed to a glucose sensor package system for sterilizing a glucose sensor using electron beam sterilization, the system including at least one glucose sensor, a protective package, and at least one radiation exposure indicator. The protective package has an interior to hold the at least one glucose sensor in the interior of the protective package. The at least one radiation exposure indicator is used to determine if the protective package has been exposed to a predetermined exposure level of electron beam sterilization. For example, preferred embodiments have the predetermined exposure level above 2.0 Mrad. Other embodiments have the predetermined exposure level less than or equal to 5.0 Mrad or above 0.5 Mrad. In further embodiments, the at least one radiation exposure indicator indicates that the predetermined exposure level existed for a period of time.

In particular embodiments, the at least one radiation exposure indicator is attached to the protective package. For example, the at least one radiation exposure indicator may be attached to the interior of the protective package, or an exterior of the protective package. In other embodiments, the at least one radiation exposure indicator may be contained within the protective package. In further embodiments, the radiation exposure indicator may be attached to the glucose sensor. Preferably, the at least one radiation exposure indicator is a sticker. Other embodiments are directed to a method of sterilizing the glucose sensor.

Still additional embodiments are directed to a glucose sensor including a substrate, a working electrode including at least one enzyme and being coupled to the substrate, a counter electrode coupled to the substrate, and a reference electrode coupled to the substrate. In preferred embodiments, the counter electrode is formed larger than the working electrode, and the working electrode is formed larger than the reference electrode. In still further embodiments, the working electrode is placed between counter electrode and the reference electrode. In additional embodiments, the glucose sensor also includes at least one attached temperature exposure indicator.

Packaged glucose sensors as described above are also provided in accordance with further embodiments. Further embodiments include at least one temperature exposure indicator attached to the packaging and/or to the glucose sensor.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

As shown in the drawings for purposes of illustration, the invention is embodied in a glucose monitor system that is coupled to a subcutaneous glucose sensor set to provide continuous data recording of the sensor readings for a period of time. In preferred embodiments of the present invention, the glucose sensor and glucose monitor are for determining glucose levels in the blood and/or bodily fluids of the user. However, it will be recognized that further embodiments of the invention may be used to determine the levels of other analytes or agents, characteristics or compositions, such as hormones, cholesterol, medications concentrations, viral loads (e.g., HIV), or the like. In other embodiments, the glucose monitor may also include the capability to be programmed to take data at specified time intervals or calibrated using an initial data input received from an external device. The glucose monitor and glucose sensor are primarily adapted for use in subcutaneous human tissue. However, still further embodiments may be placed in other types tissue, such as muscle, lymph, organ tissue, veins, arteries or the like, and used in animal tissue. Embodiments may record sensor readings on an intermittent, near continuous or continuous basis.

Due to the use of enzyme materials, or other complex chemistries, on the electrodes of the glucose sensor, it is important to maintain the glucose sensor at lower temperatures for storage and transport prior to use. Preferably, the glucose sensor is stored in a controlled temperature range of 2 to 24° C. (or 36 to 75° F.) to provide a minimum long term storage time of 6 months to 2 years. However, shorter storage times of 1 month or longer storage times of 5 years (or more) may be used. In addition, glucose sensors are preferably designed to withstand 1 hour of 45° C. (or 113° F.) without substantial de-nature of the glucose sensor enzyme or chemistries.

The best approach to assure proper temperature control is to refrigerate the glucose sensors, but not freeze them. Preferably, the glucose sensors should be shipped in temperature controlled vehicles or in individual packages that provide temperature control during transportation, such as with a cold pack, sufficient insulation to maintain temperature after removal from refrigerated storage, or the like. It is anticipated that transportation may take anywhere from a few hours to three days for the glucose sensors to arrive at their intended destination, and the temperature must be maintained below a predetermined temperature threshold during this period. In alternative embodiments, other possibly temperature sensitive materials used in the glucose sensor may also drive the selection of a temperature range or level.

To satisfy this temperature control need, embodiments of the glucose sensor and package are augmented with at least one temperature exposure indicator, such as a temperature sensitive sticker, to indicate if the glucose sensor has been exposed to excessive temperatures or has been at elevated temperatures for a predetermined period of time. The indicator, such as a dot, plate, sticker, packet, or the like, comprises a temperature-sensitive material that turns color upon exposure to elevated temperatures. Such temperature-sensitive materials are well known to those skilled in the art and are readily available commercially. Typically, temperature exposure indicators can be obtained from Wahl Instruments, Inc. of Culver City, Calif. (Part No. 442-100F), United Desiccants/Humidial of Colton, Calif. (Part No. HD11LC43), or the like.

Figure 11:
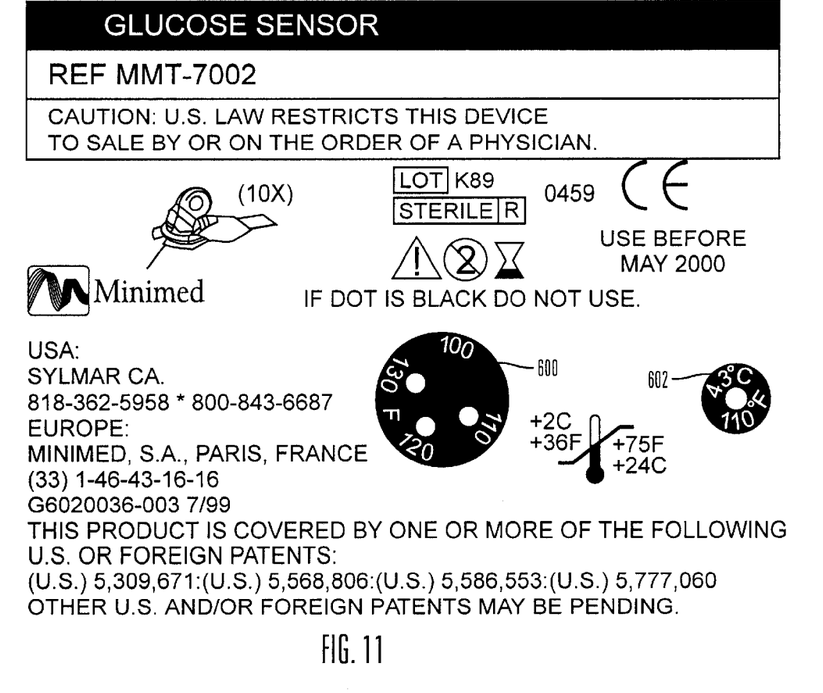
FIG. 11 is a view of a label with multiple temperature exposure indicators in accordance with an embodiment of the present invention.
Figure 12:
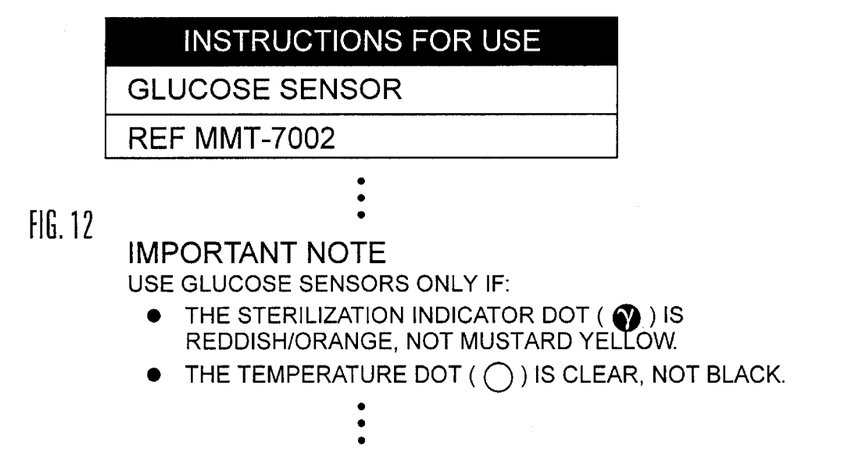
FIG. 12 is a view of a portion of an "instructions for use" in accordance with an embodiment of the present invention.

In preferred embodiments, the temperature exposure indicator turns from a white (or slight gray) to a dark gray or black after exposure to elevated temperatures. However, in alternative embodiments, other color combinations may be used. If the color change does not match the correct temperature control color, the user knows from an "instructions for use" (see FIG. 12), which preferably are supplied with the glucose sensor, not to use the glucose sensor. Preferably, the temperature exposure indicator (320, 430, 530, 600, 602) is on the exterior of the packaging to minimize any potential for contamination or reaction with the temperature indicator materials with the glucose sensor (see FIGS. 8b and 9–11). However, in alternative embodiments, the temperature exposure indicator 320 can be placed on the interior of the package (see FIG. 8a) if formed out of materials that will not interact with the glucose sensor, or if the temperature exposure indicator is contained in a sealed package that will prevent interaction with the glucose sensor. In further embodiments, multiple temperature exposure indicators on the packaging can be used (see FIGS. 10 and 11). Still further embodiments utilize temperature exposure indicators 600 that indicate exposures to a range of temperatures, such as a plurality of discrete temperature exposure indicators that are sensitive to particular temperatures (see FIG. 11).

According to further embodiments, the temperature exposure indicator indicates when the glucose sensor has been exposed to an exposure temperature exceeding a predetermined temperature, for example a temperature exceeding 100° F. (or 38° C.), for a predetermined period of time or longer, for example longer than 60 minutes, to indicate that possible degradation of the glucose materials may have occurred due to elevated temperature exposure. Alternative embodiments can indicate a change after exposure to elevated temperatures with respect to the predetermined temperature for different time periods, for example as little as a few seconds if very sensitive materials are used or a specific threshold must not be exceeded, or as long as 6 hours if generally temperature insensitive materials or better temperature-stabilized materials are used with the selection being dependent on the temperature tolerance of the glucose sensor.

In addition, other embodiments can include temperature exposure indicators that are sensitive to lower elevated temperatures, such as 80° F. (or 27° C.), 75° F. (or 24° C.), or the Like, which is closely associated with the preferred maximum long term storage temperature. If lower temperatures are used, the exposure time required to cause a change in the temperature exposure indicator can be lengthened if desired. It is also noted that the temperature exposure indicators may respond (by the color change) at more rapid rates for higher temperatures. For instance, a few minutes' exposure to 200° F. (or 93° C.) heat may cause a temperature exposure indicator (that normally takes 1 hour to change at 100° F. (or 38° C.)) to change and indicate degradation in the glucose sensor. Proper temperature control assures the user that the glucose sensors will operate properly and have not suffered degradation to the enzyme, or other temperature sensitive materials, that could effect the safe use of the device.

Thus, in particular embodiments, the temperature exposure indicator can provide an indication of exposure to exposure temperatures relative to the predetermined temperature that occur for time periods that vary with the difference between the exposure temperature and the predetermined temperature. That is, the period of time $t_e$ is a function F of a magnitude of a difference $\Delta$ between the exposure temperature $t_e$ and the predetermined temperature $t_d$. Depending on the specific temperature-sensitive material used in the temperature exposure indicator, the functional relationship can be one of proportionality, e.g., $t_e = k\Delta$, with k being a constant that is characteristic of the specific material; an exponential relationship, e.g., $t_d = k_1 \exp(k_2 \Delta)$, where $k_1$ and $k_2$ are constants; or another functional relationship. The particular functional relationship will depend on the specific temperature-sensitive material employed, and can readily be determined by the routineer without undue experimentation. In other embodiments, the temperature sensitive material changes immediately upon exposure to a temperature above a specific threshold, such that it changes in fractions of a second, seconds or after longer periods.

Figure 8A:
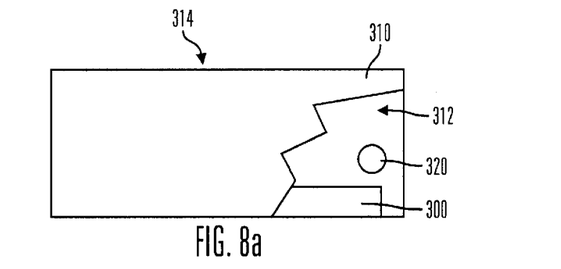
FIGS. 8a–c are perspective views, partially cut away, of embodiments of glucose sensor package systems including a protective package, a glucose sensor and a temperature exposure indicator, with the temperature exposure indicator attached to the exterior of the protective package, the interior of the protective package, and the glucose sensor, respectively.
Figure 8B:
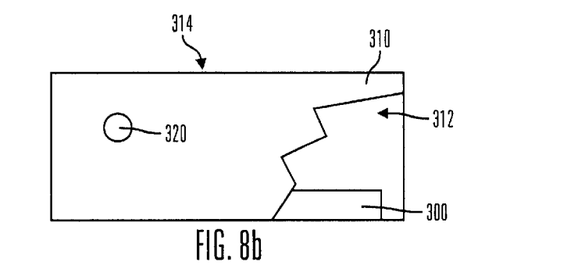
Figure 8C:
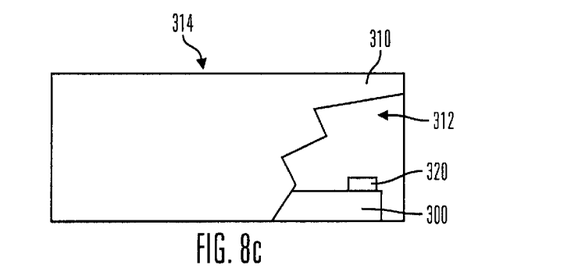

FIGS. 8a–c illustrate embodiments of a glucose sensor package system according to embodiments of the present invention including a glucose sensor 300, a protective package 310 having an interior 312 and an exterior 314, and a temperature exposure indicator 320. In FIG. 8a, glucose sensor 300 is disposed in interior 312 of protective package 310, and temperature exposure indicator 320 is attached to the interior 312 of protective package 310. In FIG. 8b, glucose sensor 300 is likewise disposed within interior 312, but a temperature exposure indicator 320 is attached to the exterior 314 of protective package 310. In FIG. 8c, a temperature exposure indicator 320 is attached directly to glucose sensor 300, which in turn is disposed within interior 312 of protective package 310.

Figure 9:
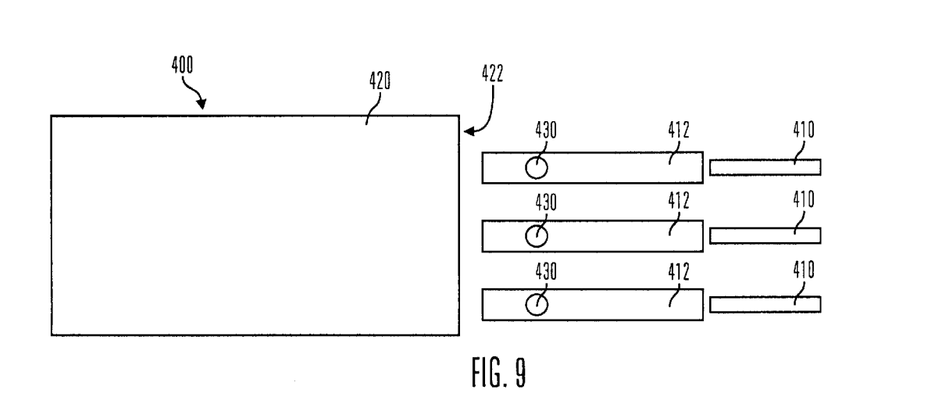
FIG. 9 is an exploded view of a glucose sensor package system that includes a plurality of individually packaged glucose sensors all disposed within a protective package, with each of the individually packaged glucose sensors having an attached temperature exposure indicator.

In FIG. 9, glucose sensor package system 400 includes a plurality of glucose sensors 410 each packaged in a separate package 412. The packaged glucose sensors 410 in turn are disposed within the interior 422 of protective package 420. A separate temperature exposure indicator 430 is affixed to each package 412. If desired, separate temperature exposure indicators can also be affixed to the protective package 420 in a manner similar to that described in connection with FIGS. 8a–b.

Figure 10:
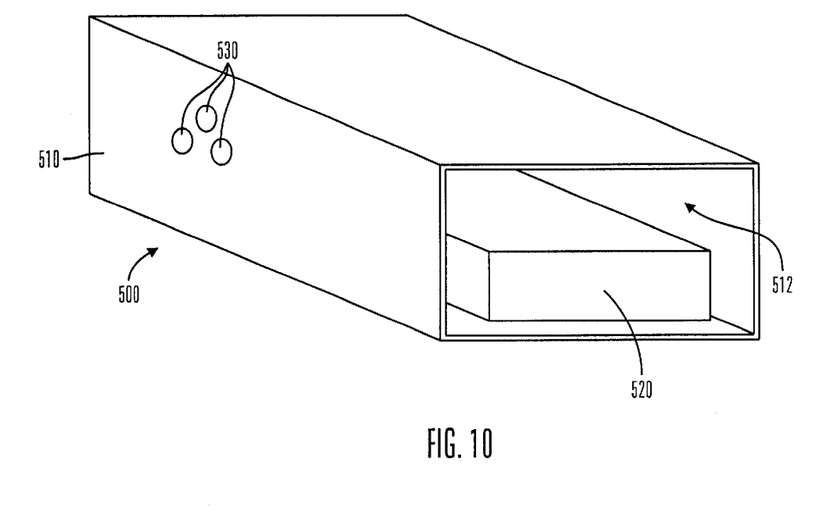
FIG. 10 is a perspective view of a glucose sensor package system including a plurality of temperature exposure indicators.

In FIG. 10, a glucose sensor package system 500 includes a protective package 510 having an interior 512 within which glucose sensor 520 is disposed. A plurality of temperature exposure indicators 530 are attached to the protective package 510. Each of the plurality of temperature exposure indicators 530 preferably provides an indication of exposure to an exposure temperature relative to a different predetermined temperature value. For example, a first temperature exposure indicator can indicate exposure to an exposure temperature relative to 80° F. (or 27° C.), 75° F. (or 24° C.), or the like, a second temperature exposure indicator can indicate exposure to an exposure temperature relative to 100° F., a third temperature exposure indicator can indicate exposure to an exposure temperature relative to 120° F. (or 49° C.), and so on. Further particular embodiments also include temperature exposure indicators that provide an indication that the exposure temperature relative to the predetermined temperature existed for a predetermined period of time.

Preferred embodiments of the glucose sensor are sterilized by electron beam sterilization with a preferred single dose of 2.0 Mrads (or 20 kGy). However, in alternative embodiments, smaller dose levels may be used if sufficient sterilization may be achieved at the lower dose, such as for example 0.5 Mads (5 kGy). Larger doses may also be used, if the glucose sensor materials are selected and assembled to withstand doses up to 5.0 Mrads (50 kGy). The glucose sensors are preferably sterilized in accordance with "ANSI/AAMI ST31-190 Guideline for Electron Beam Radiation Sterilization of Medical Devices, Method B1" and/or "ISO 11137:1995 Sterilization of Health Care Products—Validation and Routine Control—Gamma and Electron Beam Radiation Sterilization, Dose Selection Method 1", all of which are specifically incorporated by reference. The sensor materials are carefully selected with regard to housing materials, cannula materials, glucose sensor substrate, electrodes, membranes, enzyme chemistry, lubricants, insertion needle materials and the packaging materials, and manufacturing tolerances to assure the ability to withstand electron beam sterilization and the continued proper operation of the glucose sensor after sterilization. In alternative embodiments, other radiation sterilization methods, such as gamma radiation, or the like, or other chemical methods, such as ETO, or the like, may be used.

Preferred embodiments of the glucose sensor with the packaging include at least one sterilization indicator that indicates when the glucose sensor and packaging have been exposed to an electron beam sterilization procedure. The sterilization indicator, such as a dot, plate, sticker, packet, or the like, turns color upon exposure to the electron beam. In preferred embodiments, the sterilization indicator turns from a mustard yellow color or orange yellow to a red or reddish orange color after sterilization. However, in alternative embodiments, other color combinations may be used. If the color change does not match the correct sterilization color, the user knows from an "instructions for use" (see FIG. 12) not to use the glucose sensor. Preferably, the sterilization indicator is on the exterior of the packaging to minimize any potential for contamination or reaction of the sticker materials with the glucose sensor. However, in alternative embodiments, the sterilization indicator may be placed on the interior of the package if formed out of materials that will not interact with the glucose sensor or if the indicator is contained in a sealed package that will prevent interaction with the glucose sensor. In further embodiments, multiple indicators, or stickers, on the packaging may be used. Typical sterilization indicators may be obtained from NAMSA Products of Kennesaw, Ga. (Part No. CPI-RO3). In addition, the sterilization indicators can be attached to the packaging and/or glucose sensors in a manner similar to that for temperature exposure indicators as shown in FIGS. 8a–11 and described above.

Figures 13, 14:
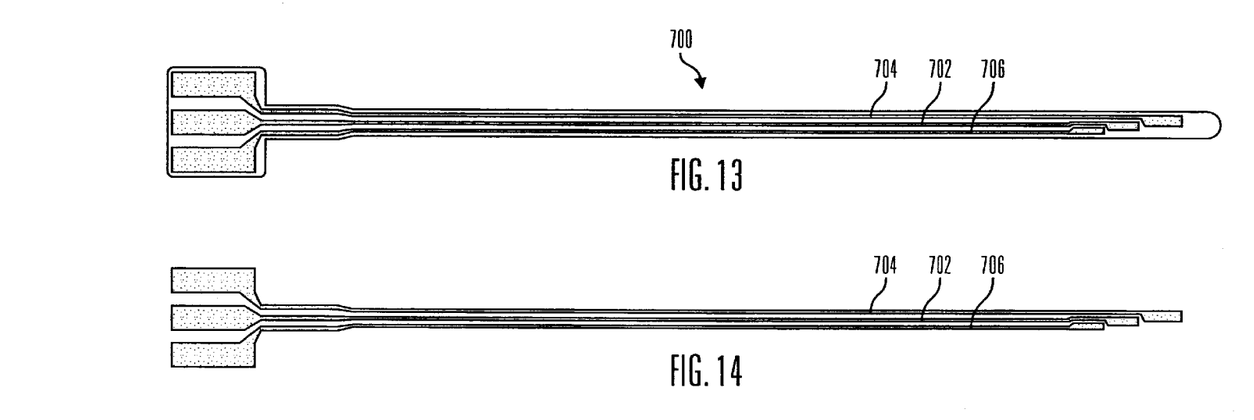
FIG. 13 is a top plan view of a sensor in accordance with an embodiment of the present invention.
FIG. 14 is a top plan view of the sensor conductors shown in FIG. 13.
Figure 15:
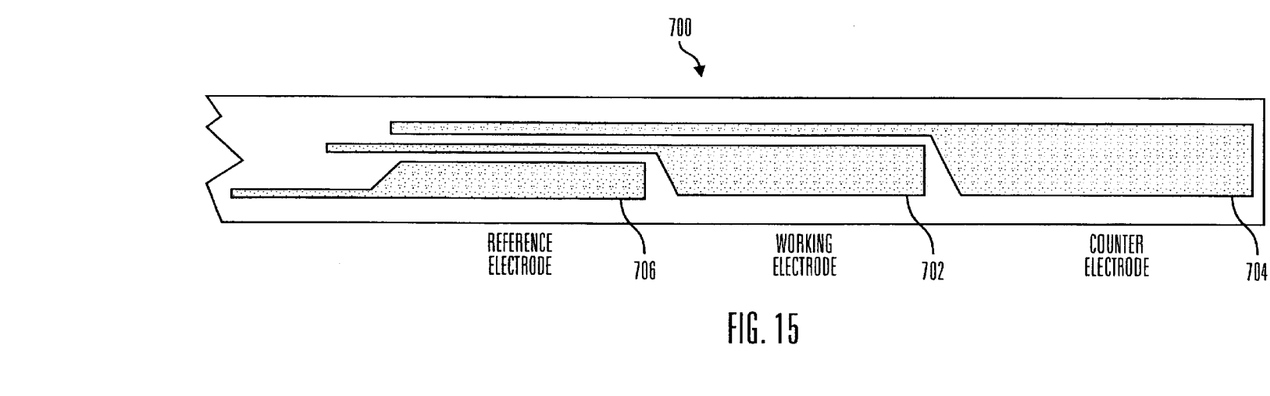
FIG. 15 is an enlarged, partial top plan view of the electrodes of the sensor shown in FIG. 13.

As shown in FIGS. 13–15, further embodiments of the glucose sensor 700 are directed towards optimizing the size, shape and orientation of the glucose sensor electrodes that come in contact with the interstitial fluid during glucose sensing. In preferred embodiments, the glucose sensor 700 includes three electrodes (a working electrode 702, a counter electrode 704 and a reference electrode 706). To optimize the electrochemistry of the glucose sensing reaction, it is preferred that the counter electrode 704 is the largest electrode, the working electrode 702 (i.e., the one with enzymes, or the like) is the next largest electrode and the reference electrode 706 is the smallest electrode. Preferably, the counter electrode 704 is as large as possible and consistent with sensor insertion requirements to minimize pain on insertion of the sensor into the body of the user. For instance, to fit within a 22 gauge needle. However, alternative embodiments may be sized to fit other gauge needles ranging from 18 gauge to 30 gauge. In addition, making the working electrode a different size effects the amount of enzyme that can be placed on the working electrode and affects the overall life of the glucose sensor. In further preferred embodiments, it has been found to optimize the current paths and the electrochemistry to have the working electrode 702 located between the counter electrode 704 and the reference electrode 706. In additional embodiments, it is preferred that the electrode (i.e., conductors) have a line width of $50\mu$ to assure good electrical conduction of a sensor signal. However, smaller widths down to $10\mu$ and anything larger can be used if a sufficient signal accuracy is provided and the sensor can fit within a needle as described above.

Additional specific embodiments of the glucose sensor include a temperature exposure indicator as described above attached directly to the sensor.

Turning again to the figures, the above may be used with the glucose monitor system 1, in accordance with a preferred embodiments of the present invention that includes a subcutaneous glucose sensor set 10, and a glucose monitor 100. The subcutaneous glucose sensor set 10 utilizes an electrode-type sensor, as described in more detail below. However, in alternative embodiments, the glucose sensor may use other types of sensors, such as chemical based, optical based or the like. In further alternative embodiments, the sensors may be of a type that is used on the external surface of the skin or placed below the skin layer of the user. Preferred embodiments of a surface mounted glucose sensor would utilize interstitial fluid harvested from the skin.

The glucose monitor 100 generally includes the capability to record and store data as it is received from the glucose sensor 10, and then includes either a data port or wireless transmitter for downloading the data to a data processor 200, computer, communication station, or the like for later analysis and review. The data processor 200, computer, or the like, utilizes the recorded data from the glucose monitor to determine the blood glucose history. Preferably, any port would be water proof (or water resistant) or include a water proof removable cover. The purpose of the glucose monitor system I is to provide for better data recording and testing for various patient conditions utilizing continuous or near continuous data recording.

The glucose monitor system 1 also removes inconvenience by separating the complicated monitoring process electronics into two separate devices; a glucose monitor 100, which attaches to the glucose sensor set 10; and a data processor 200, computer, communication station, or the like, which contains the software and programming instructions to download and evaluate data recorded by the glucose monitor 100. In addition, the use of multiple components (e.g., glucose monitor 100 and data processor 200, computer, communication station, or the like) facilitates upgrades or replacements, since one module, or the other, can be modified or replaced without requiring complete replacement of the monitor system 1. Further, the use of multiple components can improve the economics of manufacturing, since some components may require replacement on a more frequent basis, sizing requirements may be different for each module, different assembly environment requirements, and modifications can be made without affecting the other components.

The glucose monitor 100 takes raw glucose sensor data, such as glucose data or the like, from the subcutaneous glucose sensor set 10 and assesses it during real-time and/or stores it for later download to the data processor 200, computer, communication station, or the like, which in turn analyzes, displays and logs the received glucose readings. Logged data can be analyzed further for detailed data analysis. In further embodiments, the glucose monitor system 1 may be used in a hospital environment or the like. Still further embodiments of the present invention may include one or more buttons 122, 124, 126 and 128 on the glucose monitor 100 to program the monitor 100, to record data and events for later analysis, correlation, or the like. In addition, the glucose monitor may include an on/off button 130 for compliance with safety standards and regulations to temporarily suspend transmissions or recording. The glucose monitor 100 may also be combined with other medical devices to combine other patient data through a common data network and telemetry system. In alternative embodiments, the glucose monitor may be designed as a Holter-type system that includes a Holter-type recorder that interfaces with a glucose monitor, processor, computer, or the like, such as disclosed in U.S. patent application Ser. No. 09/246,661 filed Feb. 5, 1999 and entitled "An Analyte Sensor and Holter-Type Monitor System and Method of Using the Same", and U.S. patent application Ser. No. 09/377,472 filed Aug. 19, 1999 and entitled "Telemetered Characteristic Monitor System and Method of Using the Same", which are all herein incorporated by reference.

As shown in FIGS. 1–7, a glucose sensor set 10 is provided for subcutaneous placement of a flexible sensor 12 (see FIG. 2), or the like, at a selected site in the body of a user. The implantable glucose sensor set 10 includes a hollow, slotted insertion needle 14, and a cannula 16. The needle 14 is used to facilitate quick and easy subcutaneous placement of the cannula 16 at the subcutaneous insertion site. The cannula 16 includes a sensing portion 18 of the sensor 12 to expose one or more sensor electrodes 20 to the user's bodily fluids through a window 22 formed in the cannula 16. After insertion, the insertion needle 14 is withdrawn to leave the cannula 16 with the sensing portion 18 and the sensor electrodes 20 in place at the selected insertion site.

In preferred embodiments, the implantable subcutaneous glucose sensor set 10 facilitates accurate placement of a flexible thin film electrochemical sensor 12 of the type used for monitoring specific blood parameters representative of a user's condition. Preferably, the sensor 12 monitors blood glucose levels, and may be used in conjunction with automated or semi-automated medication infusion pumps of the external or implantable type as described in U.S. Pat. Nos. 4,562,751; 4,678,408; 4,685,903 or 4,573,994, to deliver insulin to a diabetic patient. However, other embodiments may monitor other analytes to determine viral load, HIV activity, bacterial levels, cholesterol levels, medication levels, or the like.

Preferred embodiments of the flexible electrochemical sensor 12 are constructed in accordance with thin film mask techniques to include elongated thin film conductors embedded or encased between layers of a selected insulative material such as polyimide film or sheet. The sensor electrodes 20 at a tip end of the sensing portion 18 are exposed through one of the insulative layers for direct contact with patient blood, or other bodily fluids, when the sensor 12 is subcutaneously placed at an insertion site. The sensing portion 18 is joined to a connection portion 24 (see FIG. 2) that terminates in conductive contact pads, or the like, which are also exposed through one of the insulative layers. In alternative embodiments, other types of implantable glucose sensors, such as chemical based, optical based, or the like, may be used.

Figures 1, 2:
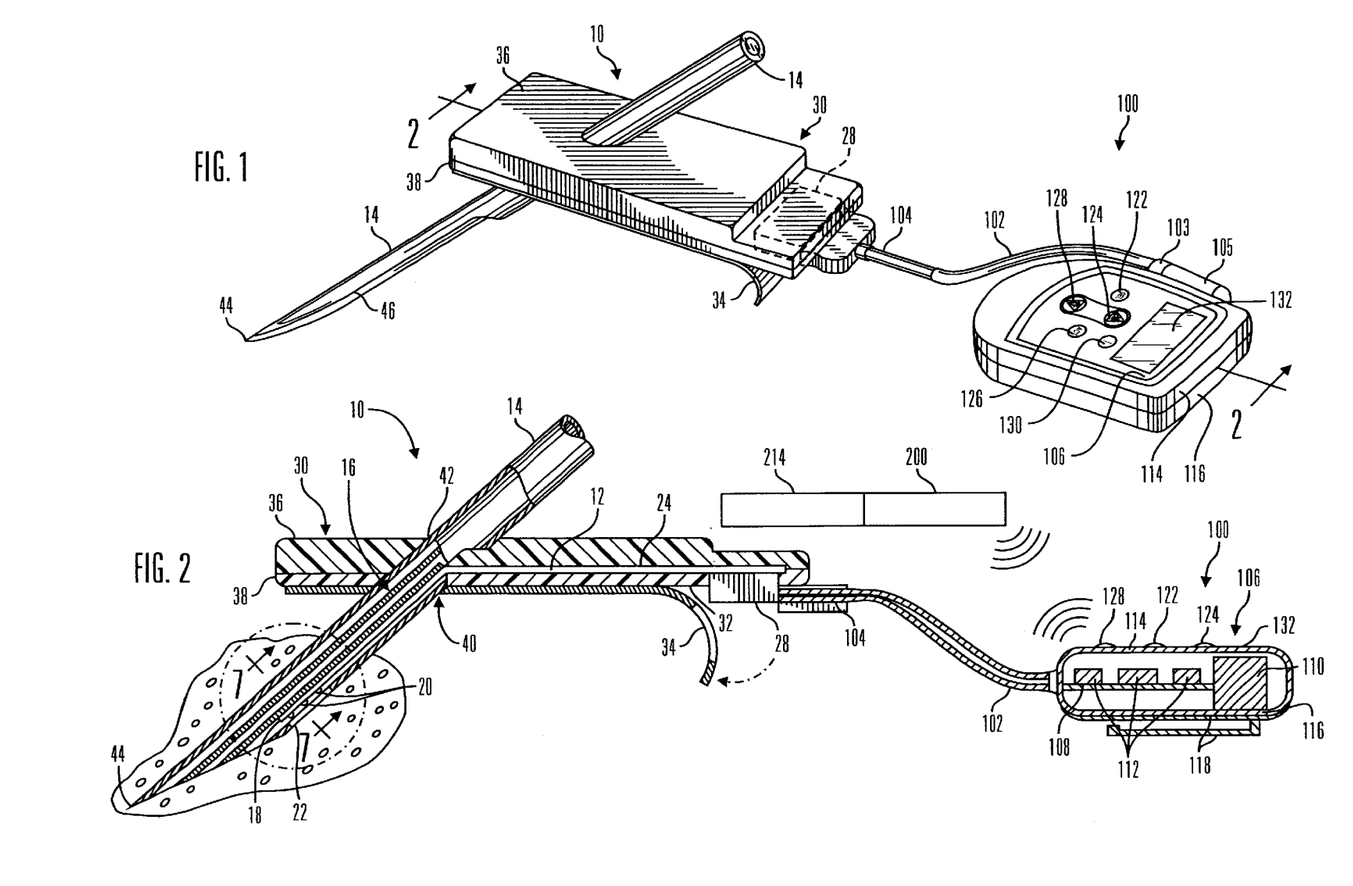
FIG. 1 is a is a perspective view illustrating a subcutaneous glucose sensor insertion set and glucose monitor device embodying the novel features of the invention.
FIG. 2 is an enlarged longitudinal vertical section taken generally on the line 2—2 of FIG. 1.
Figure 3:
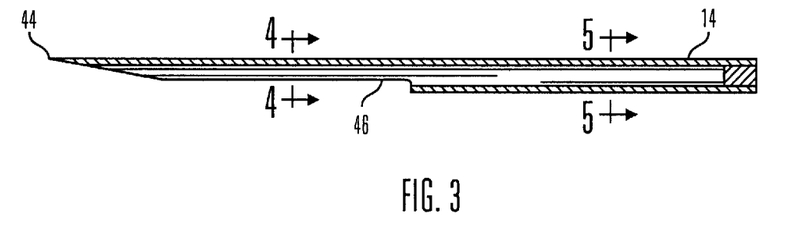
FIG. 3 is an enlarged longitudinal sectional of a slotted insertion needle used in the insertion set of FIGS. 1 and 2.
Figure 4:
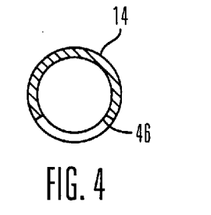
FIG. 4 is an enlarged transverse section taken generally on the line 4—4 of FIG. 3.
Figure 5:
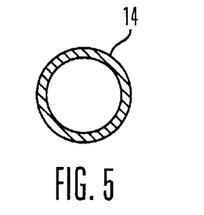
FIG. 5 is an enlarged transverse section taken generally on the line 5—5 of FIG. 3.

As is known in the art, and illustrated schematically in FIG. 2, the connection portion 24 and the contact pads are generally adapted for a direct wired electrical connection to a suitable sensor monitor for monitoring a user's condition in response to signals derived from the sensor electrodes 20. Further description of flexible thin film sensors of this general type are be found in U.S. Pat. No. 5,391,250, entitled METHOD OF FABRICATING THIN FILM SENSORS, which is herein incorporated by reference. The connection portion 24 may be conveniently connected electrically to the sensor monitor (not shown), a glucose monitor 100, or a data processor 200, computer, communication station, or the like, by a connector block 28 (or the like) as shown and described in U.S. Pat. No. 5,482,473, entitled FLEX CIRCUIT CONNECTOR, which is also herein incorporated by reference. Thus, in accordance with embodiments of the present invention, subcutaneous sensor sets 10 are configured or formed to work with either a recording, wired or a wireless system.

The sensor 12 is mounted in a mounting base 30 adapted for placement onto the skin of a user. As shown, the mounting base 30 is a generally rectangular pad having an underside surface coated with a suitable pressure sensitive adhesive layer 32, with a peel-off paper strip 34 normally provided to cover and protect the adhesive layer 32, until the sensor set 10 is ready for use. As shown in FIGS. 1 and 2, the mounting base 30 includes upper and lower layers 36 and 38, with the connection portion 24 of the flexible sensor 12 being sandwiched between the layers 36 and 38. The connection portion 24 has a forward section joined to the sensing portion 18 of the sensor 12, which is folded angularly to extend downwardly through a bore 40 formed in the lower base layer 38. In preferred embodiments, the adhesive layer 32 includes an anti-bacterial agent to reduce the chance of infection; however, alternative embodiments may omit the agent. In further alternative embodiments, the mounting base may be other shapes, such as circular, oval, hour-glass, butterfly or the like.

The insertion needle 14 is adapted for slide-fit reception through a needle port 42 formed in the upper base layer 36 and further through the lower bore 40 in the lower base layer 38. As shown, the insertion needle 14 has a sharpened tip 44 and an open slot 46 which extends longitudinally from the tip 44 at the underside of the needle 14 to a position at least within the bore 40 in the lower base layer 36. Above the mounting base 30, the insertion needle 14 may have a full round cross-sectional shape, and may be closed off at a rear end of the needle 14. Further description of the needle 14 and the sensor set 10 are found in U.S. Pat. No. 5,586,553, entitled "TRANSCUTANEOUS SENSOR INSERTION SET" and co-pending U.S. patent application Ser. No. 09/346,835 filed Jul. 2, 1999, entitled "INSERTION SET FOR A TRANSCUTANEOUS SENSOR," which are herein incorporated by reference.

Figure 6:
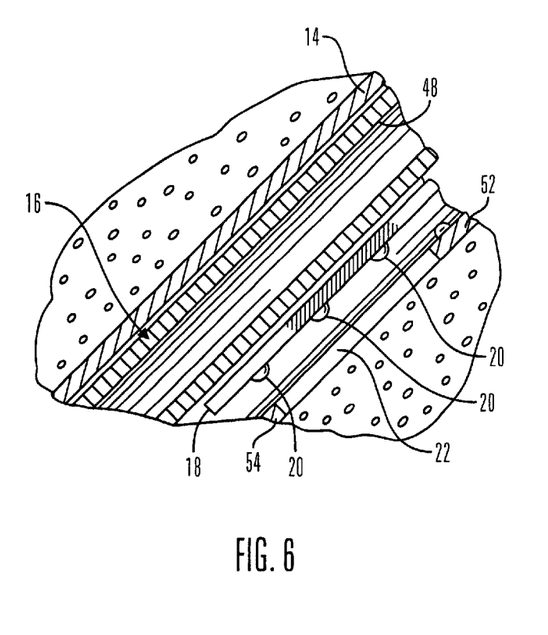
FIG. 6 is an enlarged fragmented sectional view corresponding generally with the encircled region 6 of FIG. 2.
Figure 7:
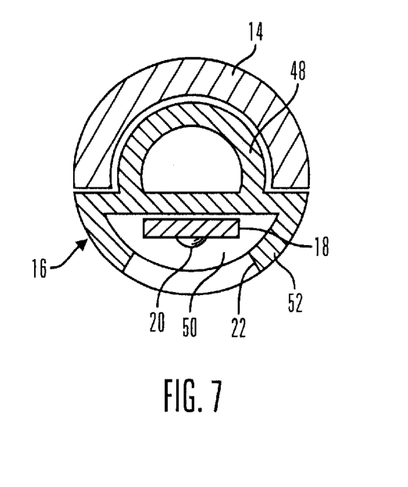
FIG. 7 is an enlarged transverse section taken generally on the line 7—7 of FIG. 2.

The cannula 16 is best shown in FIGS. 6 and 7, and includes a first portion 48 having partly-circular cross-section to fit within the insertion needle 14 that extends downwardly from the mounting base 30. In alternative embodiments, the first portion 48 may be formed with a solid core; rather than a hollow core. In preferred embodiments, the cannula 16 is constructed from a suitable medical grade plastic or elastomer, such as polytetrafluoroethylene, silicone, or the like. The cannula 16 also defines an open lumen 50 in a second portion 52 for receiving, protecting and guideably supporting the sensing portion 18 of the sensor 12. The cannula 16 has one end fitted into the bore 40 formed in the lower layer 38 of the mounting base 30, and the cannula 16 is secured to the mounting base 30 by a suitable adhesive, ultrasonic welding, snap fit or other selected attachment method. From the mounting base 30, the cannula 16 extends angularly downwardly with the first portion 48 nested within the insertion needle 14, and terminates slightly before the needle tip 44. At least one window 22 is formed in the lumen 50 near the implanted end 54, in general alignment with the sensor electrodes 20, to permit direct electrode exposure to the user's bodily fluid when the sensor 12 is subcutaneously placed.

As shown in FIGS. 1 and 2, the glucose monitor 100 is coupled to a subcutaneous glucose sensor set 10 by a cable 102 through a connector 104 that is electrically coupled to the connector block 28 of the connector portion 24 of the subcutaneous glucose sensor set 10. In preferred embodiments, the plug connector 103 of the cable 102 is connected to the glucose monitor 100 through a plug receptacle 105. In alternative embodiments, the cable 102 may be omitted, and the glucose monitor 100 may include an appropriate connector (not shown) for direct connection to the connector portion 24 of the subcutaneous glucose sensor set 10 or the subcutaneous glucose sensor set 10 may be modified to have the connector portion 24 positioned at a different location, such as for example, the top of the subcutaneous sensor set 10 to facilitate placement of the telemetered characteristic monitor transmitter over the subcutaneous sensor set 10. This would minimize the amount of skin surface covered or contacted by medical devices, and tend to minimize potential electrical interference induced by movement of the subcutaneous glucose sensor set 10 relative to the telemetered characteristic monitor transmitter 100. In further alternative embodiments, the cable 102 and the connector 104 may be formed as add-on adapters to fit different types of connectors on different types or kinds of sensor sets. The use of adapters would facilitate adaptation of the glucose monitor 100 to work with a wide variety of sensor systems.

The glucose monitor 100 includes a housing 106 that supports a printed circuit board 108, batteries 110, memory storage 112, the cable 102 with the plug connector 103, and the plug receptacle 105. In preferred embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In preferred embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In preferred embodiments, the housing 106 is generally rectangular. However, in alternative embodiments, other shapes, such as hour glass, disk, oval shaped, or the like, may be used. Preferred embodiments of the housing 106 are sized in the range of 3.0 square inches by 0.5 inches thick. However, larger or smaller sizes, such as 0.5 square inches and 0.15 inches thick or less, and 5.0 square inches and 1.0 inches thick or more, may be used.

As shown, the lower case 116 may have an underside surface that includes a belt clip 118 (or the like) to attach to a user's clothing. In other embodiments, the underside surface is coated with a suitable pressure sensitive adhesive layer, with a peel-off paper strip normally provided to cover and protect the adhesive layer, until the glucose monitor 100 is ready for use. In preferred embodiments, the adhesive layer includes an anti-bacterial agent to reduce the chance of infection; however, alternative embodiments may omit the agent. In further alternative embodiments, the glucose monitor 100 is secured to the body by other methods, such as an adhesive overdressing, straps, belts, clips or the like.

In preferred embodiments, the cable 102 should also include a flexible strain relief portion (not shown) to minimize strain on the subcutaneous sensor set 10 and prevent movement of the implanted sensor 12, which can lead to discomfort or dislodging of the glucose sensor set 10. The flexible strain relief portion is intended to minimize sensor artifacts generated by user movements that causes the subcutaneous glucose sensor set 10 to move relative to the glucose monitor 100.

The interface via the plug receptacle 105 of the glucose monitor 100 connects with the cable plug 103 of the cable 102 that is connected with the subcutaneous sensor set 10 via the connector 104. In preferred embodiments, the sensor interface may be configured in the form of a jack to accept different types of cables that provide adaptability of the glucose monitor 100 to work with different types of subcutaneous glucose sensors and/or glucose sensors placed in different locations of the user's body. However, in alternative embodiments, the sensor interface is permanently connected to the cable 102. In preferred embodiments, the printed circuit board 108, and associated electronics, are capable of operating in a temperature range of 0° C. and 50° C. However, larger or smaller temperature ranges may be used.

Preferably, the battery assembly will use a weld tab design to connect power to the system. For example, it can use three series silver oxide 357 battery cells 110, or the like. However, it is understood that different battery chemistries may be used, such as lithium, alkaline or the like, and different numbers of batteries can be used. In further embodiments, the sensor interface will include circuitry and/or a mechanism for detecting connection to the subcutaneous glucose sensor set 10. This would provide the capability to save power and to more quickly and efficiently start initialization of the subcutaneous glucose sensor set 10. In preferred embodiments, the batteries 110 have a life in the range of 3 months to 2 years, and provide a low battery warning alarm. Alternative embodiments, may provide longer or shorter battery lifetimes, or include a power port or solar cells to permit recharging of the batteries 110 in the glucose monitor 100.

In preferred embodiments, the glucose monitor 100 provides power, through plug receptacle 105 to the cable plug 103 of the cable 102 and then through the cable connector 104 to the glucose sensor set 10. The power is used to drive the glucose sensor set 10. The power connection is also used to speed the initialization of the sensor 12, when it is first placed under the skin. The use of an initialization process can reduce the time for sensor 12 stabilization from several hours to an hour or less. The preferred initialization procedure uses a two step process. First, a high voltage (preferably between 1.0–1.2 volts—although other voltages may be used) is applied to the sensor 12 for 1 to 2 minutes (although different time periods may be used) to allow the sensor 12 to stabilize. Then, a lower voltage (preferably between 0.5–0.6 volts—although other voltages may be used) is applied for the remainder of the initialization process (typically 58 minutes or less). Other stabilization/ initialization procedures using differing currents, currents and voltages, different numbers of steps, or the like, may be used. Other embodiments may omit the initialization/ stabilization process, if not required by the glucose sensor or if timing is not a factor.

At the completion of the stabilizing process, an initial reading may be downloaded from the glucose sensor set 10 and the glucose monitor 100 to the data processor 200, computer, communication station, or the like, to verify proper operation of the glucose sensor 10 and the glucose monitor 100. In alternative embodiments, a fluid containing a known value of glucose may be injected into the site around the glucose sensor set 10, and then the reading sent to the glucose monitor 100 records the data for the known value to provide a reference point to the recorded data, such as disclosed in U.S. patent application Ser. No. 09/161,128, filed Sep. 25, 1998, entitled "A SUBCUTANEOUS IMPLANTABLE SENSOR SET HAVING THE CAPABILITY TO REMOVE OR DELIVER FLUIDS TO AN INSERTION SITE," now U.S. Pat. No. 5,951,521, which is herein incorporated by reference. During the stabilization process, the glucose monitor 100 checks to determine if the glucose sensor set 10 is still connected. If the glucose sensor set 10 is no longer connected, the glucose monitor 100 will abort the stabilization process and sound an alarm (or flash a light, or download a signal to the data processor 200, computer, communication station, or the like, to sound an alarm).

In further alternative embodiments, the glucose monitor 100 can be combined with a glucose sensor set 10 as a single unit. This would be particularly well adapted where batteries and the glucose monitor 100 can be made cheaply enough to facilitate changing the glucose monitor 100 with each new glucose sensor set 10, such as in a Holter-type monitor, or the like.

As shown in FIG. 2, the data processor 200, computer, communication station, or the like, may include a display 214 that is used to display the results of the measurement received from the sensor 18 in the glucose sensor set 10 received via a download from the glucose monitor 100. The results and information displayed includes, but is not limited to, trending information of the characteristic (e.g., rate of change of glucose), graphs of historical data, average characteristic levels (e.g., glucose), or the like. Alternative embodiments include the ability to scroll through the data. The display 214 may also be used with buttons (not shown) on the data processor 200, computer, communication station, or the like, characteristic monitor to program or update data in the data processor 200. In preferred embodiments, the glucose monitor 100 includes a display 132 to assist the user in programming the glucose monitor 100, entering data, stabilizing, calibrating, downloading data, or the like.

In further embodiments of the present invention, the data processor 200, computer, communication station, or the like, may be replaced by a different device. For example, in one embodiment, the glucose monitor 100 communicates with an RF programmer (not shown) that is also used to program and obtain data from an infusion pump or the like. The RF programmer may also be used to update and program the glucose monitor 100, if the glucose monitor 100 includes a receiver for remote programming, calibration or data receipt. The RF programmer can be used to store data obtained from the sensor 18 and then provide it to either an infusion pump, characteristic monitor, computer or the like for analysis. In further embodiments, the glucose monitor 100 may transmit the data to a medication delivery device, such as an infusion pump or the like, as part of a closed loop system. This would allow the medication delivery device to compare sensor results with medication delivery data and either sound alarms when appropriate or suggest corrections to the medication delivery regimen. In preferred embodiments, the glucose monitor 100 would include a transmitter to receive updates or requests for additional sensor data. An example of one type of RF programmer can be found in U.S. patent application Ser. No. 09/334,858 filed Jun. 17, 1999 and is entitled "INFUSION DEVICE WITH REMOTE PROGRAMMING, CARBOHYDRATE CALCULATOR AND/OR VIBRATION ALARM CAPABILITIES," which is herein incorporated by reference.

Additional embodiments of the present invention may include a vibrator alarm (or optical indicator such as an L.E.D.) in the either, or both, the glucose monitor 100 to provide a tactile (vibration) alarm to the user, so as to indicate a glucose sensor set malfunction, improper connection, low battery, missed message, bad data, interference, or the like. The use of a vibration alarm provides additional reminders to an audio alarm, which could be important with someone suffering an acute reaction, or to have non-audio alarms to preserve and conceal the presence of the glucose monitor.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A glucose sensor package system for storing and transporting a glucose sensor, the system comprising:
   at least one glucose sensor, comprising a plurality of glucose sensors each of which is enclosed within a separate packages
   a protective package having an interior within which the at least one glucose sensor is disposed and an exterior, the plurality of packaged glucose sensors in turn being disposed within the interior of the protective package; and
   a temperature exposure indicator that has first and second states, the first state indicating that the protective package has not been exposed to an exposure temperature relative to a predetermined temperature value, the second state indicating that the protective package has been exposed to the exposure temperature.

2. The glucose sensor package system according to claim 1, wherein the exposure temperature is above the predetermined temperature, and wherein the temperature exposure indicator indicates exposure to the exposure temperature.

3. The glucose sensor package system according to claim 2, wherein the predetermined temperature is 75° F. and the exposure temperature exceeds 75° F.

4. The glucose sensor package system according to claim 2, wherein the predetermined temperature is 100° F. and the exposure temperature exceeds 100° F.

5. The glucose sensor package system according to claim 1, wherein the exposure temperature is below the predetermined temperature, and wherein the temperature exposure indicator indicates exposure to the exposure temperature.

6. The glucose sensor package system according to claim 5, wherein the predetermined temperature is 36° F. and the exposure temperature is below 36° F.

7. The glucose sensor package system according to claim 1, wherein the temperature exposure indicator indicates that the exposure temperature relative to the predetermined temperature existed for a predetermined period of time.

8. The glucose sensor package system according to claim 7, wherein the period of time is established as a function of a magnitude of a difference between the exposure temperature and the predetermined temperature.

9. The glucose sensor package system according to claim 7, wherein the period of time is at least 10 minutes.

10. The glucose sensor package system according to claim 9, wherein the period of time is at least 60 minutes.

11. The glucose sensor package system according to claim 1, wherein the temperature exposure indicator is attached to the protective package.

12. The glucose sensor package system according to claim 11, wherein the temperature exposure indicator is attached to the interior of the protective package.

13. The glucose sensor package system according to claim 11, wherein the temperature exposure indicator is attached to an exterior of the protective package.

14. The glucose sensor package system according to claim 1, wherein the temperature exposure indicator is contained within the protective package.

15. The glucose sensor package system according to claim 1, wherein the temperature exposure indicator is a sticker.

16. The glucose sensor package system according to claim 1, wherein the exposure temperature exceeds the predetermined temperature.

17. The glucose sensor package system according to claim 16, wherein the predetermined temperature is 75° F.

18. The glucose sensor package system according to claim 16, wherein the predetermined temperature is 100° F.

19. The glucose sensor package system according to claim 1, wherein the exposure temperature is below the predetermined temperature.

20. The glucose sensor package system according to claim 19, wherein the predetermined temperature is 36° F.

21. The glucose sensor package system according to claim 1, wherein the temperature exposure indicator further indicates exposure to the exposure temperature for a predetermined period of time.

22. The glucose sensor package system according to claim 21, wherein the predetermined period of time has a length that is determined as a function of a magnitude of a difference between the exposure temperature and the predetermined temperature.

23. The glucose sensor package system according to claim 21, wherein the length of the predetermined period of time is at least 10 minutes.

24. The glucose sensor package system according to claim 23, wherein the length of the predetermined period of time is at least 60 minutes.

25. The glucose sensor package system according to claim 1, wherein the temperature exposure indicator is attached to the protective package.

26. The glucose sensor package system according to claim 25, wherein the temperature exposure indicator is attached to the interior of the protective package.

27. The glucose sensor package system according to claim 25, wherein the temperature exposure indicator is attached to the exterior of the protective package.

28. The glucose sensor package system according to claim 1, wherein the temperature exposure indicator is contained within the protective package.

29. The glucose sensor package system of claim 1 comprising a plurality of temperature exposure indicators each of which is attached to one of the separate packages.

30. A glucose sensor package system for storing and transporting a glucose sensor, the system comprising:
   at least one glucose sensor;
   a protective package having an interior to hold the at least one glucose sensor in the interior of the protective package; and
   a temperature exposure indicator to determine if the protective package has been exposed to an exposure temperature relative to a predetermined temperature value, wherein the temperature exposure indicator is attached to the glucose sensor.

31. A method of transporting a glucose sensor, the method comprising the steps of:
   a) providing a glucose sensor package system including
      i) at least one glucose sensor, wherein the glucose sensor package system comprises a plurality of glucose sensors each of which is enclosed within separate packages,
      ii) a protective package having an interior within which the at least one glucose sensor is disposed and an exterior, the plurality of packaged glucose sensors in turn being disposed within the interior of the protective package; and
      iii) a temperature exposure indicator that has first and second states, the first state indicating that the protective package has not been exposed to an exposure temperature relative to a predetermined temperature value, the second state indicating that the protective package has been exposed to the exposure temperature; and
   b) transporting the glucose sensor packaging system, and
   c) observing the state of the temperature exposure indicator to determine if the protective package has been exposed to the exposure temperature during transport.

32. The method according to claim 31, wherein the exposure temperature is above the predetermined temperature, and further using the temperature exposure indicator to indicate exposure to the exposure temperature above the predetermined temperature.

33. The method according to claim 32, wherein the predetermined temperature is 75° F. and the exposure temperature exceeds 75° F.

34. The method according to claim 32, wherein the predetermined temperature is 100° F. and the exposure temperature exceeds 100° F.

35. The method according to claim 31, wherein the exposure temperature is below the predetermined temperature, and further using the temperature exposure indicator to indicate exposure to the exposure temperature below the predetermined temperature.

36. The method according to claim 35, wherein the predetermined temperature is 36° F. and the exposure temperature is below 36° F.

37. The method according to claim 31, further using the temperature exposure indicator to indicate that the exposure temperature relative to the predetermined temperature existed for a predetermined period of time.

38. The method according to claim 37, wherein the period of time is established as a function of a magnitude of a difference between the exposure temperature and the predetermined temperature.

39. The method according to claim 37, wherein the period of time is at least 10 minutes.

40. The method according to claim 39, wherein the period of time is at least 60 minutes.

41. The method according to claim 31, further comprising the step of attaching the temperature exposure indicator to the protective package.

42. The method according to claim 41, further comprising the step of attaching the temperature exposure indicator to the interior of the protective package.

43. The method according to claim 41, further comprising the step of attaching the temperature exposure indicator to an exterior of the protective package.

44. The method according to claim 31, further comprising the step of containing the temperature exposure indicator within the protective package.

45. The method according to claim 31, further comprising using the temperature exposure indicator formed as a sticker.

46. The method according to claim 31, wherein the exposure temperature is above the predetermined temperature.

47. The method according to claim 46, wherein the predetermined temperature is 75° F.

48. The method according to claim 46, wherein the predetermined temperature is 100° F.

49. The method according to claim 48, wherein the predetermined temperature is 36° F.

50. The method according to claim 31, wherein the exposure temperature is below the predetermined temperature.

51. The method according to claim 31, wherein the temperature exposure indicator further provides an indication that the exposure temperature relative to the predetermined temperature existed for a predetermined period of time.

52. The method according to claim 51, wherein the predetermined period of time has a length that is determined as a function of a magnitude of a difference between the exposure temperature and the predetermined temperature.

53. The method according to claim 51, wherein the length of the predetermined period of time is at least 10 minutes.

54. The method according to claim 53, wherein the length of the predetermined period of time is at least 60 minutes.

55. The method according to claim 31, wherein the temperature exposure indicator is attached to the protective package.

56. The method according to claim 53, wherein the temperature exposure indicator is attached to the interior of the protective package.

57. The method according to claim 53, wherein the temperature exposure indicator is attached to the exterior of the protective package.

58. The method according to claim 31, wherein the temperature exposure indicator is contained within the protective package.

59. The method according to claim 31, wherein the glucose sensor package system comprises a plurality of temperature exposure indicators each of which is attached to one of the separate packages.

60. A method of transporting a glucose sensor, the method comprising the steps of:
   a) providing at least one glucose sensor;
   b) providing a protective package having an interior;
   c) holding the at least one glucose sensor in the interior of the protective package; and
   d) using a temperature exposure indicator to determine if the protective package has been exposed to an exposure temperature relative to a predetermined temperature value, further comprising the step of attaching the temperature exposure indicator to the glucose sensor.

61. A glucose sensor package system for storing and transporting a glucose sensor, the system comprising:
- at least one glucose sensor;
- a protective package having an interior within which the at least one glucose sensor is disposed and an exterior; and
- a temperature exposure indicator that has first and second states, the first state indicating that the protective package has not been exposed to an exposure temperature relative to a predetermined temperature value, the second state indicating that the protective package has been exposed to the exposure temperature wherein the temperature exposure indicator is attached to the glucose sensor.

62. A glucose sensor package system for storing and transporting a glucose sensor, the system comprising:
- at least one glucose sensor;
- a protective package having an interior within which the at least one glucose sensor is disposed and an exterior; and
- a temperature exposure indicator that has first and second states, the first state indicating that the protective package has not been exposed to an exposure temperature relative to a predetermined temperature value, the second state indicating that the protective package has been exposed to the exposure temperature, comprising a plurality of temperature exposure indicators each of which provides an indication of exposure to an exposure temperature relative to a different predetermined temperature value.

63. A method of transporting a glucose sensor, the method comprising the steps of:
a) providing a glucose sensor package system including
   i) at least one glucose sensor,
   ii) a protective package having an interior within which the at least one glucose sensor is disposed and an exterior; and
   iii) a temperature exposure indicator that has first and second states, the first state indicating that the protective package has not been exposed to an exposure temperature relative to a predetermined temperature value, the second state indicating that the protective package has been exposed to the exposure temperature: and
b) transporting the glucose sensor packaging system, and
c) observing the state of the temperature exposure indicator to determine if the protective package has been exposed to the exposure temperature during transport, wherein the temperature exposure indicator is attached to the glucose sensor.

64. A method of transporting a glucose sensor, the method comprising the steps of:
a) providing a glucose sensor package system including
   i) at least one glucose sensor,
   ii) a protective package having an interior within which the at least one glucose sensor is disposed and an exterior; and
   iii) a temperature exposure indicator that has first and second states, the first state indicating that the protective package has not been exposed to an exposure temperature relative to a predetermined temperature value, the second state indicating that the protective package has been exposed to the exposure temperature; and
b) transporting the glucose sensor packaging system, and
c) observing the state of the temperature exposure indicator to determine if the protective package has been exposed to the exposure temperature during transport, wherein the glucose sensor package system comprises a plurality of temperature exposure indicators each of which provides an indication of exposure to an exposure temperature relative to a different predetermined temperature value, and wherein in step c) the state of each temperature exposure indicator is observed to determine if the protective package has been exposed to an exposure temperature relative to at least one of the different predetermined values.

* * * * *